US012577193B2

(12) United States Patent
Bitsch-Larsen et al.

(10) Patent No.: US 12,577,193 B2
(45) Date of Patent: Mar. 17, 2026

(54) PROCESS FOR RECOVERING OXIDATION BY-PRODUCTS

(71) Applicant: Ineos US Chemicals Company, Naperville, IL (US)

(72) Inventors: Anders Bitsch-Larsen, Naperville, IL (US); Gang Jia, Zhuhai City (CN)

(73) Assignee: Ineos US Chemicals Company, Naperville, IL (US)

( * ) Notice: Subject to any disclaimer, the term of this patent is extended or adjusted under 35 U.S.C. 154(b) by 374 days.

(21) Appl. No.: 18/008,757

(22) PCT Filed: Sep. 27, 2020

(86) PCT No.: PCT/CN2020/118010
§ 371 (c)(1),
(2) Date: Dec. 7, 2022

(87) PCT Pub. No.: WO2022/061793
PCT Pub. Date: Mar. 31, 2022

(65) Prior Publication Data
US 2023/0219878 A1 Jul. 13, 2023

(51) Int. Cl.
*C07C 67/58* (2006.01)
*B01D 3/14* (2006.01)
(Continued)

(52) U.S. Cl.
CPC .............. *C07C 67/58* (2013.01); *B01D 3/145* (2013.01); *B01D 5/006* (2013.01);
(Continued)

(58) Field of Classification Search
CPC ....... C07C 51/265; C07C 63/26; C07C 51/42; C07C 67/58; C07C 7/144; C07C 29/86;
(Continued)

(56) References Cited

U.S. PATENT DOCUMENTS

| | | | |
|---|---|---|---|
| 4,329,493 A | 5/1982 | Hashizume et al. | |
| 5,013,424 A | 5/1991 | James, Jr. et al. | |

(Continued)

FOREIGN PATENT DOCUMENTS

| | | |
|---|---|---|
| JP | 4431813 B2 | 3/2010 |
| WO | 96/39595 A1 | 12/1996 |

(Continued)

OTHER PUBLICATIONS

International Search Report and Written Opinion of International Application No. PCT/CN2020/118010, mailed Jun. 25, 2021, 13 pages.

*Primary Examiner* — Deborah D Carr
(74) *Attorney, Agent, or Firm* — McDonnell Boehnen Hulbert & Berghoff LLP

(57) ABSTRACT

A process for recovering by-products of a substituted aromatic hydrocarbon oxidation reaction, comprising cooling one or more of a vapor stream directed to a high-pressure absorber (380), a solvent-rich scrubbing stream (381) directed to a high-pressure absorber (380), and a water-rich liquid stream (383) directed to a solvent recovery zone, by heat exchange with a cooled spent scrubbing liquid withdrawn from a low-pressure scrubber (430).

20 Claims, 2 Drawing Sheets

(51) Int. Cl.

| | | |
|---|---|---|
| *B01D 5/00* | (2006.01) | |
| *B01D 53/14* | (2006.01) | |
| *C07C 7/144* | (2006.01) | |
| *C07C 29/86* | (2006.01) | |
| *C07C 51/265* | (2006.01) | |
| *C07C 51/48* | (2006.01) | |

(52) U.S. Cl.
CPC ..... *B01D 53/1406* (2013.01); *B01D 53/1425* (2013.01); *B01D 53/1493* (2013.01); *C07C 7/144* (2013.01); *C07C 29/86* (2013.01); *C07C 51/265* (2013.01); *C07C 51/48* (2013.01); *B01D 2252/103* (2013.01); *B01D 2257/2022* (2013.01)

(58) Field of Classification Search
CPC ........ C07C 51/48; B01D 3/145; B01D 5/006; B01D 53/1406; B01D 53/1425; B01D 53/1493; B01D 2252/103; B01D 2257/2022; Y02P 20/50
See application file for complete search history.

(56) References Cited

U.S. PATENT DOCUMENTS

| | | |
|---|---|---|
| 5,961,942 A | 10/1999 | Turner et al. |
| 10,173,957 B2 | 1/2019 | Peterson et al. |

FOREIGN PATENT DOCUMENTS

| | | | | |
|---|---|---|---|---|
| WO | 2006102459 A1 | 9/2006 | | |
| WO | 2018158672 A | 9/2018 | | |
| WO | 2019005532 A1 | 1/2019 | | |
| WO | WO-2020102639 A1 * | 5/2020 | ........... | C07C 51/265 |

* cited by examiner

1

PROCESS FOR RECOVERING OXIDATION BY-PRODUCTS

CROSS-REFERENCE TO RELATED APPLICATIONS

This application is a U.S. national phase application of International Patent Application No. PCT/CN2020/118010, filed Sep. 27, 2020, which is hereby incorporated herein by reference in its entirety.

TECHNICAL FIELD

The present disclosure relates generally to processes for recovering oxidation by-products. The present disclosure relates more particularly to processes for recovering by-products of a substituted aromatic hydrocarbon oxidation reaction.

TECHNICAL BACKGROUND

Terephthalic acid and other aromatic carboxylic acids are widely used in manufacture of polyesters, commonly by reaction with ethylene glycol, higher alkylene glycols or combinations thereof, for conversion to fiber, film, containers, bottles and other packaging materials, and molded articles.

In commercial practice, aromatic carboxylic acids are commonly made by liquid phase oxidation in an aqueous monocarboxylic acid solvent (e.g., acetic acid) of substituted (e.g., methyl-substituted) benzene and naphthalene feedstocks, in which the positions of the substituents (e.g., methyl substituents) correspond to the positions of carboxyl groups in the desired aromatic carboxylic acid product, with air or another source of oxygen, which is normally gaseous, in the presence of a bromine-promoted catalyst comprising cobalt and manganese. The oxidation is exothermic and yields a crude reaction mixture including aromatic carboxylic acid together with by-products including partial or intermediate oxidation products of the aromatic feedstock, water, acetic acid, and acetic acid reaction products such as methanol, methyl acetate, and methyl bromide. Terephthalic acid in particular is typically made using a para-xylene-containing feedstock.

By-products can be recovered from various process streams such as, for example, vapor- and liquid-phase effluents of the oxidation reactor and downstream crystallizers, purification reactors, and solid-liquid separators. While recovery efficiency can be improved by lowering the temperature of such streams, the temperatures achievable in conventional manufacturing processes are limited to a few degrees warmer than the temperature of the cooling water utilized elsewhere in the process. And the equipment and operating costs associated with a separate chilled water loop significantly outweigh the benefits of lowered recovery temperature.

Accordingly, there remains a need for improved processes for recovering by-products of a substituted aromatic hydrocarbon oxidation reaction.

SUMMARY OF THE INVENTION

The scope of the present disclosure is not affected to any degree by the statements within the summary.

In one aspect, the disclosure provides a process for recovering by-products of a substituted aromatic hydrocarbon oxidation reaction, comprising

2 in a low-pressure scrubber, contacting a first water-rich scrubbing stream with a first vapor stream comprising bromine to form a cooled spent stream and a first scrubbed vapor stream, the first scrubbed vapor stream comprising a reduced amount of bromine relative to the first vapor stream;

the process further comprising one or both of a) in a high-pressure absorber, contacting a second vapor stream comprising one or more by-products of the substituted aromatic hydrocarbon oxidation reaction with a second solvent-rich scrubbing stream to form a second scrubbed vapor stream, the second scrubbed vapor stream comprising a reduced amount of one or more by-products relative to the second vapor stream, wherein, before introduction to the high-pressure absorber, at least one of the second vapor stream and the second solvent-rich scrubbing stream is cooled by heat-exchange with at least a portion of the cooled spent stream; and b) in a solvent recovery zone, separating at least a portion of a water-rich liquid stream comprising one or more by-products of the substituted aromatic hydrocarbon oxidation reaction by reverse osmosis to form a by-product stream and a purified stream, the purified stream comprising a reduced amount of one or more by-products relative to the water-rich liquid stream, wherein, before introduction to the solvent recovery zone, the water-rich liquid stream is cooled by heat-exchange with at least a portion of the cooled spent stream.

In certain embodiments as otherwise described herein, the process further comprises transferring (e.g., directly or indirectly) at least a portion of a liquid effluent of the high-pressure absorber including one or more by-products of the substituted aromatic hydrocarbon oxidation reaction to a reaction zone capable of performing the substituted aromatic hydrocarbon oxidation reaction.

In certain embodiments as otherwise described herein, the process further comprises contacting the second vapor stream with a second water-rich scrubbing stream in the high-pressure absorber.

In certain embodiments as otherwise described herein, the process comprises cooling, by heat exchange with at least a portion of the cooled spent stream, the second vapor stream to form a cooled second vapor stream; and then contacting the cooled second vapor stream with the second solvent-rich scrubbing stream in the high-pressure absorber.

In certain embodiments as otherwise described herein, the process further comprises in a reaction zone, oxidizing a feedstock comprising a substituted aromatic hydrocarbon in the presence of an oxidation catalyst and monocarboxylic acid solvent under reaction conditions suitable to form crude aromatic carboxylic acid;

in a fractionation zone, separating at least a portion of a vapor effluent of the reaction zone to form a bottoms stream and a vapor overhead stream, the vapor overhead stream comprising steam and one or more additional by-products of the substituted aromatic hydrocarbon oxidation reaction;

in a condensing zone, condensing a portion of the vapor overhead stream to form a water-rich condensate; and cooling at least a portion of a vapor effluent of the condensing zone including one or more by-products to form the second vapor stream.

3                                                              4

In certain embodiments as otherwise described herein, cooling at least a portion of the vapor effluent comprises heat-exchange with a coolant stream having a temperature that is at least 2° C. (e.g., at least 3° C.) higher than the temperature of the cooled spent stream.

In certain embodiments as otherwise described herein, the process comprises cooling, by heat exchange with at least a portion of the cooled spent stream, the second solvent-rich scrubbing stream to form a cooled second solvent-rich scrubbing stream; and then contacting the second vapor stream with the cooled second solvent-rich scrubbing stream in the high-pressure absorber.

In certain embodiments as otherwise described herein, the process further comprises cooling at least a portion of a liquid effluent of a solvent drum (e.g., containing acetic acid) to form the second solvent-rich scrubbing stream.

In certain embodiments as otherwise described herein, cooling at least a portion of the liquid effluent comprises heat-exchange with a coolant stream having a temperature that is at least 2° C. (e.g., at least 3° C.) higher than the temperature of the cooled spent stream.

In certain embodiments as otherwise described herein, the process comprises cooling, by heat exchange with at least a portion of the cooled spent stream, the water-rich liquid stream to form a cooled water-rich liquid stream; and then separating the cooled water-rich liquid stream by reverse osmosis in the solvent recovery zone.

In certain embodiments as otherwise described herein, the process further comprises transferring (e.g., directly or indirectly) at least a portion of the byproduct stream including one or more by-products of the substituted aromatic hydrocarbon oxidation reaction to a reaction zone capable of performing the substituted aromatic hydrocarbon oxidation reaction.

In certain embodiments as otherwise described herein, the process further comprises in a reaction zone, oxidizing a feedstock comprising a substituted aromatic hydrocarbon in the presence of an oxidation catalyst and monocarboxylic acid solvent under reaction conditions suitable to form crude aromatic carboxylic acid;

in a fractionation zone, separating at least a portion of a vapor effluent of the reaction zone to form a bottoms stream and a vapor overhead stream, the vapor overhead stream comprising steam and one or more additional by-products of the substituted aromatic hydrocarbon oxidation reaction;

in a condensing zone, condensing a portion of the vapor overhead stream to form a water-rich condensate comprising one or more by-products; and cooling at least a portion of the water-rich condensate including one or more by-products to form the water-rich liquid stream.

In certain embodiments as otherwise described herein, the first vapor stream comprises at least a portion of the second scrubbed vapor stream.

In certain embodiments as otherwise described herein, the process further comprises in a preheating zone, heating at least a portion of the second scrubbed vapor stream to form a preheated vapor stream;

in an oxidation unit, oxidizing at least a portion of the preheated vapor stream to produce an oxidized high-pressure vapor stream; and in an expander, expanding at least a portion of the oxidized high-pressure vapor stream to form the first vapor stream.

In certain embodiments as otherwise described herein, the process further comprises releasing at least a portion of the first scrubbed vapor stream to atmosphere.

In certain embodiments as otherwise described herein, the first water-rich scrubbing stream has a temperature of 32-43° C.

In certain embodiments as otherwise described herein, the temperature of the cooled spent stream is at least 2° C. (e.g., at least 3° C.) lower than the temperature of the first water-rich scrubbing stream.

In certain embodiments as otherwise described herein, the substituted aromatic hydrocarbon oxidation reaction is oxidation of para-xylene to form terephthalic acid.

In certain embodiments as otherwise described herein, the one or more by-products include acetic acid, methyl acetate, methanol, and/or para-xylene.

In another aspect, the disclosure provides a system for recovering by-products of a substituted aromatic hydrocarbon oxidation reaction, comprising a low-pressure scrubber capable of contacting a first water-rich scrubbing stream with a first vapor stream comprising bromine to form a cooled spent stream and a first scrubbed vapor stream, the first scrubbed vapor stream comprising a reduced amount of bromine relative to the first vapor stream;

the system further comprising one or both of a) a high-pressure absorber capable of contacting a second vapor stream comprising one or more by-products of the substituted aromatic hydrocarbon oxidation reaction with a second solvent-rich scrubbing stream to form a second scrubbed vapor stream, the second scrubbed vapor stream comprising a reduced amount of one or more by-products relative to the second vapor stream, and at least one of a heat exchanger capable of cooling the second vapor stream before introduction to the high-pressure absorber, by heat exchange with at least a portion of the cooled spent stream; and a heat exchanger capable of cooling the second solvent-rich scrubbing stream before introduction to the high-pressure absorber, by heat exchange with at least a portion of the cooled spent stream; and b) a reverse osmosis unit capable of separating at least a portion of a water-rich liquid stream comprising one or more by-products of the substituted aromatic hydrocarbon oxidation reaction by reverse osmosis to form a by-product stream and a purified stream, the purified stream comprising a reduced amount of the one or more by-products relative to the water-rich liquid stream, and a heat exchanger capable of cooling the water-rich liquid stream before introduction to the recovery zone, by heat exchange with at least a portion of the cooled spent stream.

DETAILED DESCRIPTION

Figure 1:
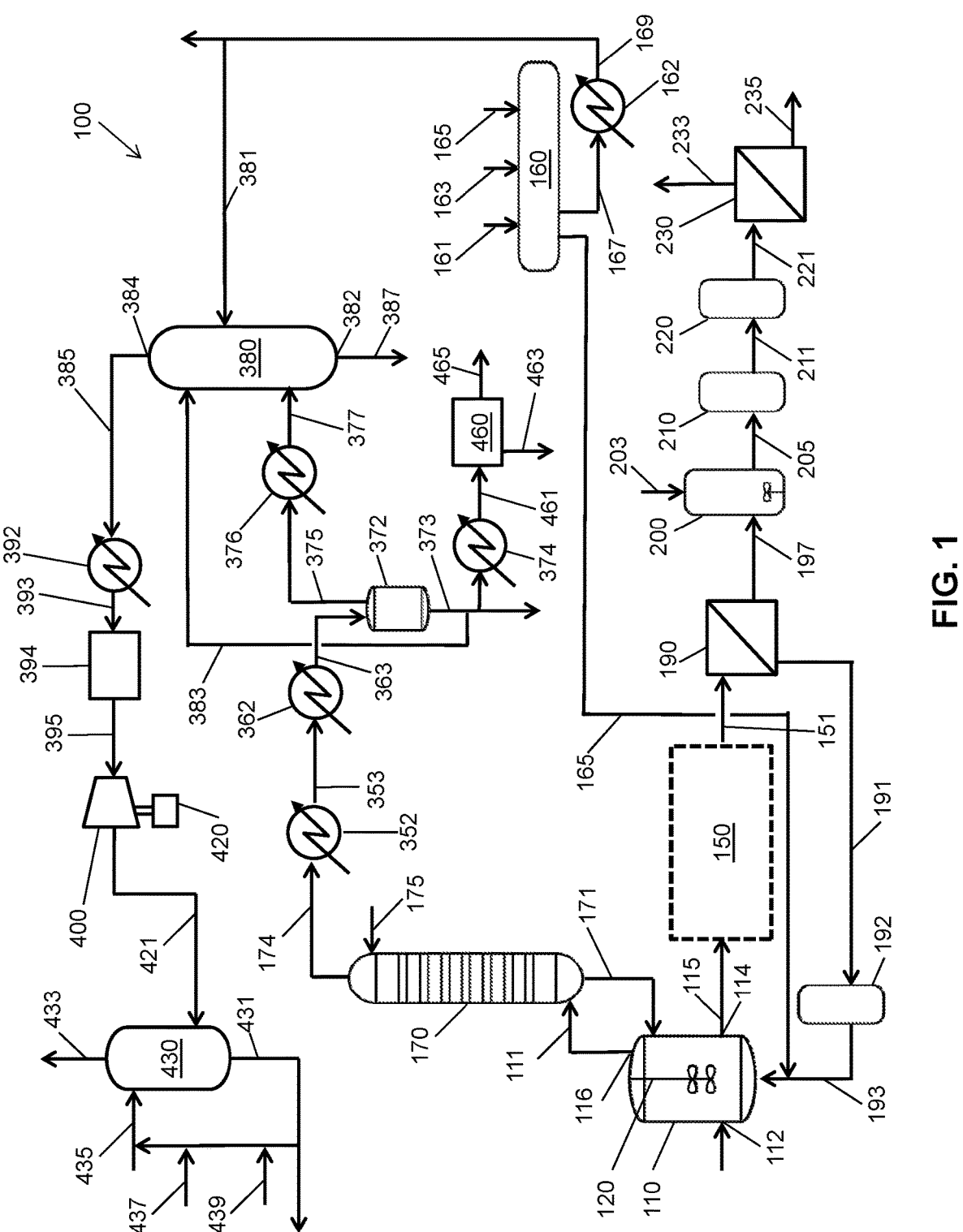
FIG. 1 is a process flow diagram depicting an integrated process including recovering by-products of a substituted aromatic hydrocarbon oxidation reaction according to certain embodiments of the disclosure.

In various aspects, the processes of the disclosure provide an improved process for recovery of one or more by-products of a substituted aromatic hydrocarbon oxidation reaction.

Additional features of the processes of the disclosure will now be described in reference to the drawing figures.

The present inventors have determined that certain by-products of a substituted aromatic hydrocarbon oxidation reaction (e.g., acetic acid, methyl acetate, para-xylene) can be more efficiently recovered by cooling one or more streams directed to a high-pressure absorber (e.g., configured to scrub a portion of the vapor-phase overhead of the oxidation reaction) or a solvent recovery zone (e.g., configured to separate a condensed portion of the vapor-phase overhead of the oxidation reaction by reverse osmosis) by heat-exchange with spent scrubbing liquid withdrawn from a low-pressure scrubber (e.g., configured to scrub process off-gas). Advantageously, due to partial evaporation in the low-pressure scrubber, the temperature of the spent scrubbing liquid can be several degrees cooler than that of cooling liquid utilized elsewhere in the process (e.g., to cool the scrubbing liquid directed to the low-pressure scrubber). Utilizing the spent scrubbing liquid as coolant elsewhere in an integrated process can advantageously improve recovery of one or more useful compounds (e.g., for recycle to aromatic hydrocarbon oxidation reaction).

Accordingly, one aspect of the disclosure provides a process for recovering by-products of a substituted aromatic hydrocarbon oxidation reaction comprising, in a low-pressure scrubber, contacting a water-rich scrubbing stream with a first vapor stream comprising bromine to form a cooled spent stream and a first scrubbed vapor stream, the first scrubbed vapor stream comprising a reduced amount of bromine relative to the first vapor stream. The process further comprises one or both of (a) in a high-pressure absorber, contacting a second vapor stream comprising one or more by-products of the substituted aromatic hydrocarbon oxidation reaction with a second solvent-rich scrubbing stream to form a second scrubbed vapor stream, the second scrubbed vapor stream comprising a reduced amount of one or more by-products relative to the second vapor stream wherein, before introduction to the high-pressure absorber, at least one of the second vapor stream and the second solvent-rich scrubbing stream is cooled by heat-exchange with at least a portion of the cooled spent stream; and (b) in a solvent recovery zone, separating at least a portion of a water-rich liquid stream comprising one or more by-products of the substituted aromatic hydrocarbon oxidation reaction by reverse osmosis to form a by-product stream and a purified stream, the purified stream comprising a reduced amount of one or more by-products relative to the water-rich liquid stream, wherein before introduction to the solvent recovery zone, the water-rich liquid stream is cooled by heat-exchange with at least a portion of the cooled spend stream. For example, in certain embodiments as otherwise described herein, the process includes the contacting in the high-pressure absorber step (a) described above. In certain embodiments as otherwise described herein, the process includes the separating in the solvent recovery zone step (b) described above, in certain embodiments as otherwise described herein, the process includes both the contacting in the high-pressure absorber step (a) described above and the separating in the solvent recovery zone step (b) described above.

As used herein, "by-products" of a substituted aromatic hydrocarbon oxidation reaction include any components of the reaction mixture other than the desired reaction product (e.g., an aromatic carboxylic acid). As the person of ordinary skill in the art will appreciate, an effluent of a substituted aromatic hydrocarbon oxidation reaction can accordingly include an aromatic carboxylic acid reaction product and by-products such as water, solvent (e.g., monocarboxylic acid such as acetic acid), solvent reaction products, starting material (e.g., substituted aromatic hydrocarbon), partial and intermediate oxidation products, and catalyst. For example, by-products of a para-xylene oxidation reaction can include para-xylene, acetic acid, and acetic acid reaction products (e.g., methanol, methyl acetate, methyl bromide).

A "high-pressure absorber" is configured to operate at a higher pressure Than a "low-pressure scrubber," e.g., at least 2 barg higher pressure, or at least 3 barg higher pressure than a low-pressure scrubber. In certain embodiments as otherwise described herein, a "low-pressure scrubber" operates at a pressure in the range of 0-0.5 barg. In certain embodiments as otherwise described herein, a "high-pressure absorber" operates a pressure in the range of 6-15 barg (e.g., 9-12 barg).

FIG. 1 is a process flow diagram depicting an integrated process for manufacturing and recovering aromatic carboxylic acids including recovering by-products of a substituted aromatic hydrocarbon oxidation reaction in accordance with one embodiment of the present disclosure. A system for performing a process 100 of FIG. 1 includes a reaction zone that includes an oxidation reactor 110 configured for liquid-phase oxidation of feedstock to provide a liquid effluent and a vapor effluent; a crystallization zone 150 configured for forming solid crude aromatic carboxylic acid from the liquid effluent, and comprising one or more crystallizers in series; a solid/liquid separation device 190 configured for separating solid crude aromatic carboxylic acid (and oxidation by-products) from liquid; a mixing zone including a purification reaction mixture make-up vessel 200 configured for preparing mixtures of crude aromatic carboxylic acid in purification reaction solvent; a purification zone including a hydrogenation reactor 210 configured for contacting the crude aromatic carboxylic acid with hydrogen in the presence of a catalyst to form a purified aromatic carboxylic acid; a recovery zone comprising a crystallizer 220 configured for forming a slurry stream comprising solid purified aromatic carboxylic acid and a vapor stream; and a solid/liquid separation device 230 configured for separating solid purified aromatic carboxylic acid from liquid.

The system of FIG. 1 also includes a fractionation zone that includes a distillation column 170 configured to separate the vapor effluent of the reaction zone to provide a bottoms stream and a vapor overhead stream, a condensing zone that includes condensers 352, 362 and a drum 372, configured for condensing the vapor overhead stream to provide a water-containing condensate and vapor effluent, a high-pressure absorber 380 (e.g., configured to operate at a pressure of 6-15 barg) configured for recovering by-products of the oxidation reaction from the vapor effluent of the drum 372 and forming a scrubbed gas stream. The system further includes an emission control zone including preheater 392 and oxidation unit 394 configured for forming an oxidized high-pressure gas; an expander 400 connected to generator 420 configured for converting energy from the oxidized high-pressure gas to electrical energy and forming an expanded gas; and a low-pressure scrubber 430 (e.g., configured to operate at a pressure of 0-0.5 berg) configured for recovering by-products of the oxidation reaction from the expanded gas.

However, the person of ordinary skill in the art will appreciate that the integration of processes in FIG. 1 is meant to be purely representative, and various other integrated and non-integrated configurations may likewise be used. Liquid and vapor streams and materials used in the process represented in FIG. 1 may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams of compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

As described above, the integrated process of FIG. 1 includes an emissions control zone including low-pressure scrubber 430. In operation, a bromine-containing first vapor stream 421 (e.g., comprising a vapor effluent of expander 400) is contacted in low-pressure scrubber 430 with a first water-rich scrubbing stream 435 to form a first scrubbed vapor stream 433 comprising a reduced amount of bromine (i.e., relative to first vapor stream 421) and a cooled spent stream 431. In certain embodiments as otherwise described herein, the first water-rich scrubbing stream is contacted with the first vapor stream at a pressure of no more than 0.5 barg (e.g., 0-0.25 barg). In certain embodiments as otherwise described herein, the first scrubbed vapor stream is released to atmosphere.

In the embodiment of FIG. 1, the first water-rich scrubbing stream 435 includes a portion of the cooled spent stream 431, combined with one or more make-up streams 437, 439 (e.g., including water and one or more of sodium hydroxide, sodium carbonate, sodium bicarbonate, sodium bromide, sodium formate, sodium sulphite, etc.). In certain embodiments, a portion of the cooled spent stream 431 is transferred (not shown) to a wastewater treatment zone (e.g., including one or more of aerobic treatment and anaerobic treatment) to produce a treated wastewater stream that can be released to the environment.

In certain embodiments as, otherwise described herein, the temperature of the first water-rich scrubbing stream (e.g., at an inlet of the low-pressure scrubber) is at least 30° C., for example, at least 32 C. For example, in certain such embodiments, the temperature of the first water-rich scrubbing stream is in the range of 32-43° C., or 32-39° C., or 32-37° C. For example, in certain such embodiments, the water-rich scrubbing stream is cooled to a temperature of 32-43° C. by heat exchange with a coolant comprising process cooling water having a temperature of 30-40° C.

The present inventors note that, due to partial evaporation in the low-pressure scrubber, the temperature of the spent scrubbing liquid can be several degrees cooler than that of cooling liquid utilized elsewhere in the process (e.g., to cool the scrubbing liquid directed to the low-pressure scrubber), and accordingly can be used to cool one or more process streams to a temperature lower than achievable with typical process cooling water. Accordingly, in certain embodiments as otherwise described herein, the temperature of the cooled spent stream is at least 2° C. (e.g., at least 3° C.) lower than the temperature of the first water-rich scrubbing stream.

In certain embodiments as otherwise described herein, the first water-rich scrubbing stream is substantially water (e.g., comprises at least 80 wt. %, or at least 90 wt. %, or at least 95 wt % water). In certain embodiments, the first water-rich scrubbing stream comprises water, present in an amount of at least 90 wt. % (e.g., at least 95 wt. %), and one or more of one or more of sodium hydroxide, sodium carbonate, sodium bicarbonate, sodium bromide, sodium formate, and sodium sulphite, present in a combined amount of at least 0.5 wt. % (e.g., 1-5 wt. %). In certain embodiments as otherwise described herein, the cooled spent stream comprises at least 80 wt. %, e.g., at least 90 wt. %, or at least 95 wt. % water.

Returning now to the integrated process of FIG. 1, a reaction mixture including a feedstock including a substituted aromatic hydrocarbon, a monocarboxylic acid solvent, water, an oxidation catalyst, and a promoter is contacted with oxygen gas in oxidation reactor 110 under conditions sufficient to cause oxidation of the substituted aromatic hydrocarbon to an aromatic carboxylic acid. In certain embodiments as otherwise described herein, the temperature and pressure of the oxidation reaction are sufficient to maintain in the reaction zone a liquid-phase reaction mixture and a high-temperature, high-pressure vapor phase. In certain embodiments as otherwise described herein, the reaction zone includes one or more pressure-rated, continuous-stirred tank reactors.

The feedstock including a substituted aromatic hydrocarbon is introduced into the oxidation reactor 110 through one or more inlets, such as inlet 112. In certain embodiments as otherwise described herein, the feedstock includes an aromatic hydrocarbon substituted at one or more positions with at least one substituent that is oxidizable to a carboxylic acid group. In some embodiments, the positions of the substituents correspond to the positions of the carboxylic acid groups of the aromatic carboxylic acid being prepared. In some embodiments, the oxidizable substituents include alkyl groups (e.g., methyl, ethyl, and/or isopropyl groups). In other embodiments, the oxidizable substituents include oxygen-containing groups, such as hydroxyalkyl, formyl, aldehyde, and/or keto groups. The substituents may be the same or different. The aromatic portion of feedstock compounds may be a benzene nucleus or it may be bi- or polycyclic (e.g., a naphthalene and/or anthracene nucleus). In some embodiments, the number of oxidizable substituents on the aromatic portion of the feedstock compound is equal to the number of sites available on the aromatic portion. In other embodiments, the number of oxidizable substituents on the aromatic portion of the feedstock is fewer than all such sites (e.g., in some embodiments 1 to 4 and, in some embodiments, 2). In certain embodiments as otherwise described herein, the feedstock includes one or more compounds selected from toluene; ethylbenzene and other alkyl-substituted benzenes; o-xylene; p-xylene; m-xylene; tolualdehydes, toluic acids, alkyl benzyl alcohols, 1-formyl-4-methylbenzene, 1-hydroxymethyl-4-methylbenzene; methylacetophenone: 1,2,4-trimethylbenzene; 1-formyl-2,4-dimethyl-benzene; 1,2,4,5-tetramethylbenzene; alkyl-, formyl-, acyl-, and hydroxylmethyl-substituted naphthalenes (e.g., 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl ethylnaphthalene, and the like); and partially oxidized derivatives thereof.

In some embodiments, the substituted aromatic compound comprises a methyl-, ethyl-, and/or isopropyl-substituted aromatic hydrocarbon. In some embodiments, the substituted aromatic compound comprises an alkyl-substituted benzene, ortho-xylene, para-xylene, meta-xylene, or the like, or combinations thereof. In certain desirable embodiments, the feedstock includes para-xylene, and the aromatic carboxylic acid reaction product is terephthalic acid. For example, in certain embodiments as otherwise described herein, a feedstock comprising at least 99 wt. % para-xylene is continuously charged to the oxidation reactor.

Water, monocarboxylic acid solvent, catalyst, promoter, and an oxygen source are also each introduced (e.g., alone or in any combination) into the oxidation reactor 110 through one or more inlets, such as inlet 112. In certain embodiments as otherwise described herein, the monocarboxylic acid solvent is acetic acid. In certain such embodiments, an aqueous acetic acid solution (e.g., comprising 70-95 wt. % acetic acid) is continuously charged to the oxidation reactor. In certain embodiments as otherwise described herein, the oxidation catalyst comprises at least one heavy metal component (e.g., selected from Co, Mn, V, Mo, Cr, Fe, Ni, Zi, Ce, Hf, etc.). For example, in certain embodiments, the oxidation catalyst includes soluble compounds of cobalt and manganese (e.g., cobalt acetate and manganese acetate). In certain such embodiments, cobalt acetate and manganese acetate are continuously charged to the oxidation reactor. In certain embodiments as otherwise described herein, the promoter includes a halogen (e.g., bromine). In certain such embodiments, hydrogen bromide is continuously charged to the oxidation reactor. In certain embodiments as otherwise described herein, the oxygen source is air. In certain such embodiments, air is continuously charged to oxidation reaction vessel.

In the embodiment of FIG. 1, stirring is provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

As described above, oxidation of the substituted aromatic hydrocarbon produces an aromatic carboxylic acid. In certain embodiments as otherwise described herein, the aromatic carboxylic acid is a mono- or polycarboxylated species having one or more aromatic rings. In some embodiments, the aromatic carboxylic acid comprises only one aromatic ring. In other embodiments, the aromatic carboxylic acid comprises a plurality (e.g., two or more) of aromatic rings that, in some embodiments, are fused (e.g., naphthalene, anthracene, etc.) and, in other embodiments, are not. In some embodiments, the aromatic carboxylic acid comprises only one carboxylic acid (e.g., —CO₂H) moiety or a salt thereof (e.g., —CO₂X, where X is a cationic species including but not limited to metal cations, ammonium ions, and the like). In other embodiments, the aromatic carboxylic acid comprises a plurality (e.g., two or more) of carboxylic acid moieties or salts thereof. In certain embodiments as otherwise described herein, the aromatic carboxylic acid is selected from terephthalic acid, trimesic acid, trimellitic acid, phthalic acid, isophthalic acid, benzoic acid, naphthalene dicarboxylic acids, and combinations thereof.

In certain embodiments as otherwise described herein, the substituted aromatic hydrocarbon is para-xylene, and the oxidation reaction product is terephthalic acid. In certain such embodiments, the oxidation reaction produces one or more partial or intermediate oxidation products such as, for example, 4-carboxybenzaldehyde, 1,4-hydroxymethyl benzoic acid, p-toluic acid, benzoic acid. In certain such embodiments, the high-temperature, high-pressure vapor phase contained in the reactor comprises one or more of monocarboxylic acid solvent (e.g., acetic acid) and reaction products thereof (e.g., methyl acetate, methanol), steam, para-xylene and partial or intermediate oxidation products thereof, bromine and reaction products thereof (e.g., methyl bromide) carbon oxides, nitrogen (e.g., from the air charged to the reactor), and unreacted oxygen.

In the embodiment of FIG. 1, liquid-phase reaction mixture 115 is removed from reaction vessel 110 through slurry outlet 114 and transferred to one or more in-series crystallizers of crystallization zone 150, to form solid oxidation product. Conventional methods can be used in the operation of the crystallization zone. Cooling in the crystallizers may be accomplished by pressure release. One or more of the crystallizers may be vented to remove vapor resulting from pressure let down and generation of steam from the flashed vapor to a heat exchanger (not shown). A variety of process operations can be used in recovery of the crystallized carboxylic acid. In certain embodiments as otherwise described herein, at least a portion of an effluent of a last crystallizer of the crystallization zone is separated to form an aromatic carboxylic acid-rich stream and a solvent-rich stream.

A slurry stream 151 from the crystallization zone 150 including solid product is transferred to a solid-liquid separation device 190 and separated to form a solvent-rich stream 191 and an aromatic carboxylic acid-rich stream 197 comprising crude solid product. In some embodiments, the separation device is a centrifuge, a rotary vacuum filter, or a pressure filter. In some embodiments, the separation device comprises a pressure filter configured for solvent exchange (e.g., by positive displacement under pressure of mother liquor in a filter cake with wash liquid comprising water).

The solvent-rich stream 191 is collected in mother-liquor drum 192. The aromatic carboxylic acid-rich stream 197 is directed to a mixing zone including a reaction mixture make-up vessel 202. Stream 197 is mixed and slurried in make-up vessel 202 with a make-up solvent stream 203 introduced to vessel 202 to form a purification reaction mixture 205 comprising crude aromatic carboxylic acid. In some embodiments, the make-up solvent contains water. In certain embodiments as otherwise described herein, the solvent comprises a portion of a water-rich condensate formed in the condensing zone. In other embodiments, the solvent comprises a liquid-phase stream formed in a downstream solid-liquid separator.

Purification reaction mixture 205 is introduced to purification reactor 210 of the purification zone. The purification zone may further include a pump and one or more heat exchangers (not shown) configured to pre-heat the purification mixture introduced to the purification reactor. In some embodiments, the purification reactor is a hydrogenation reactor and purification in the purification reactor comprises contacting the purification reaction mixture comprising crude aromatic carboxylic acid with hydrogen in the presence of a hydrogenation catalyst.

A purification effluent 211 comprising purified aromatic carboxylic acid is withdrawn from hydrogenation reactor 210 and transferred to a crystallizer 220 of a crystallization zone downstream of the purification zone. In some embodiments, the crystallization zone includes two or more in-series crystallizers. In some embodiments, purified aromatic carboxylic acid and reduced levels of impurities are crystallized from the purification effluent.

The solid/liquid mixture 221 comprising purified carboxylic acid solids formed in crystallization zone 220 is transferred to a solid-liquid separation device 230 and separated, to form a liquid-phase stream 233 and an aromatic carboxylic acid-rich stream 235 comprising solid purified aromatic carboxylic acid.

A vapor effluent 111 comprising one or more by-products of the substituted aromatic hydrocarbon oxidation reaction is withdrawn from the oxidation reactor 110 through vent 116. In certain embodiments as otherwise described herein, the vapor effluent comprises one or more by-products selected from monocarboxylic acid solvent and reaction products thereof, steam, para-xylene and partial or intermediate oxidation products thereof, bromine and reaction products thereof, carbon oxides, nitrogen, and unreacted oxygen. For example, in certain embodiments, the vapor effluent comprises one or more by-products selected from acetic acid, methyl acetate, methanol, steam, para-xylene and partial or intermediate oxidation products thereof, methyl bromide, carbon oxides, nitrogen, and unreacted oxygen.

The vapor effluent 111 is introduced to distillation column 170 and separated to produce a bottoms stream 171 and a vapor overhead stream 174 comprising steam and one or more additional by-products of the substituted aromatic hydrocarbon oxidation reaction. In certain embodiments as otherwise described herein, the bottoms stream comprises monocarboxylic acid. In certain such embodiments, the bottoms stream includes acetic acid. For example, in certain embodiments as otherwise described herein, the bottoms stream comprises at least 70 wt. % (e.g., at least 75 wt. %, or at least 80 wt. %, or at least 85 wt. %, or at least 90 wt. %, or at least 95 wt. %) acetic acid. In certain embodiments, the bottoms stream further comprises up to 25 wt. % water (e.g., 5-20 wt. %, or 10-20 wt. %, or 15-20 wt. % water). In certain embodiments, the bottoms stream further comprises up to 5 wt. % (e.g., up to 2.5 wt. %, or up to 1 wt. %) of one or more additional by-products selected from monocarboxylic acid solvent reaction products, para-xylene and partial or intermediate oxidation products thereof, and bromine and reaction products thereof. For example, in certain embodiments as otherwise described herein, the bottoms stream comprises at least 70 wt. % (e.g., at least 75 wt. %, or at least 80 wt. %) acetic acid, up to 25 wt. % (e.g., 5-20 wt. %, or 15-20 wt. %) water, up to 1 wt. % (e.g., 0.1-1 wt. %, or 0.1-0.5 wt. %) methyl acetate. In certain such embodiments, the bottom stream comprises up to 0.5 wt % of methanol and/or methyl bromide.

In certain embodiments as otherwise described herein, the vapor overhead stream comprises steam and one or more additional by-products selected from monocarboxylic acid solvent and reaction products thereof, para-xylene and partial or intermediate oxidation products thereof, bromine and reaction products thereof, carbon oxides, nitrogen, and unreacted oxygen. For example, in certain embodiments, the vapor overhead stream comprises steam and one or more additional by-products selected from acetic acid, methyl acetate, methanol, para-xylene and partial or intermediate oxidation products thereof, methyl bromide, carbon oxides, nitrogen, and unreacted oxygen. In certain embodiments as otherwise described herein, the vapor overhead stream comprises 20-80 wt. % (e.g., 40-80 wt. %, or 45-70 wt. %) steam. In certain embodiments as otherwise described herein, the vapor overhead stream comprises one or more of nitrogen, oxygen, carbon oxides, para-xylene, methyl acetate, methanol, and acetic acid, present in a combined amount of 20-80 wt. % (e.g., 20-60 wt. %, or 30-55 wt. %) of the stream. For example, in certain such embodiments, the vapor overhead stream comprises water, present in amount of 40-80 wt. % (e.g., 45-70 wt. %), one or more of nitrogen, oxygen, and carbon oxides, present in a combined amount of 20-60 wt. % (e.g., 30-55 wt. %) and one or more of acetic acid, methyl acetate, para-xylene, and methanol, present in a combined amount of 0.1-10 wt. % (e.g., 0.5-5 wt. %).

The bottoms stream 171 is returned to the oxidation reactor 110. In the condensing zone, the vapor overhead stream 174 is partially condensed in a first condenser 352 and then in a second condenser 362 to produce a stream 363 including a water-rich condensate and uncondensed vapor, which is collected in drum 372. In certain embodiments as otherwise described herein, at least 50 wt. % (e.g., at least 60 wt. %, or at least 70 wt. %, or at least 80 wt %, or at least 90 wt. %) of steam present in the vapor overhead stream is condensed in the condensing zone. In certain embodiments as otherwise described herein, the water-rich condensate comprises at least 80 wt. % (e.g., at least 90 wt. %, or at least 95 wt. %) water. In certain embodiments as otherwise described herein, the water-rich condensate comprises monocarboxylic acid solvent (e.g., acetic acid). For example, in certain such embodiments, the water-rich condensate comprises 1-20 wt. % (e.g., 1-15 wt. %, or 1-10 wt. %, or 1-5 wt. %) acetic acid. In certain embodiments, the water-rich condensate further comprises one or more monocarboxylic acid solvent reaction products (e.g., methyl acetate and/or methanol). In certain such embodiments, the water-rich condensate comprises 1-10 wt. % (e.g., 1-7.5 wt. %, or 1-5 wt. %) methyl acetate and/or methanol.

In the embodiment of FIG. 1, a vapor effluent 375 withdrawn from drum 372 is cooled in a heat exchanger 376 to form a second vapor stream 377. Accordingly, in certain embodiments as otherwise described herein, the second vapor stream comprises at least a portion of a vapor effluent of the condensing zone. In certain embodiments as otherwise described herein, the second vapor stream comprises one or more by-products of the substituted aromatic hydrocarbon oxidation reaction selected from monocarboxylic acid solvent and reaction products thereof, para-xylene and partial or intermediate oxidation products thereof, bromine and reaction products thereof, carbon oxides, nitrogen, and unreacted oxygen. For example, in certain embodiments, the second vapor stream comprises one or more by-products selected from acetic acid, methyl acetate, methanol, para-xylene and partial or intermediate oxidation products thereof, methyl bromide, carbon oxides, nitrogen, and unreacted oxygen. In certain embodiments as otherwise described herein, the second vapor stream comprises one or more of para-xylene, methyl acetate, and acetic acid, present in a combined amount of 1-20 wt. % (e.g., 5-20 wt. %, or 5-15 wt. %, or 10-20 wt. %, or 15-20 wt. %) of the stream. In certain embodiments as otherwise described herein, the second vapor stream is substantially free from steam (e.g., comprises less than 1 wt. %, or less than 0.5 wt. %, or even less than 0.1 wt. % steam).

In certain embodiments as otherwise described herein, cooling at least a portion of the vapor effluent comprises heat-exchange with a coolant stream having a temperature that is at least 2° C. (e.g., at least 3° C.) higher than the temperature of the cooled spent stream. In certain embodiments, the coolant stream comprises process cooling water having a temperature of 30-40° C. (e.g., 30-36° C., or 30-34° C.). The present inventors note that such temperatures, typical of process cooling water, limit the achievable temperature of the second vapor stream to temperatures higher than 30° C., for example, 32-43° C., or 32-39° C., or 32-37° C.

Advantageously, the present inventors have determined that by cooling the second vapor stream by heat-exchange with the cooled spent stream from the low-pressure scrubber, recovery of by-products of the substituted aromatic hydrocarbon oxidation reaction (e.g., acetic acid, methyl acetate, para-xylene) from the vapor stream in a high-pressure absorber can be improved. Accordingly, in certain embodiments as otherwise described herein, the process includes cooling, by heat exchange with at least a portion of the cooled spent stream, the second vapor stream to form a cooled second vapor stream, and then contacting the cooled second vapor stream with a second solvent-rich scrubbing stream in the high-pressure absorber. In certain such embodiments, the temperature of the cooled second vapor stream is at most 30° C. (e.g., 22-29° C., or 22-28° C., or 22-27° C.).

In certain embodiments as otherwise described herein, a warmed spent stream (i.e., comprising the heat-exchanged product of the cooled spent stream) is recycled to the low-pressure scrubber (e.g., to low-pressure scrubber 430, as make-up stream 439). In other embodiments, the warmed spent stream is transferred to a wastewater treatment zone.

In the embodiment of FIG. 1, solvent drum 160 contains a solvent-rich liquid fraction. A condensed overhead vapor stream (not shown) of one or more crystallizers of crystallization zone 150, a condensed overhead vapor stream of mother-liquor drum 192, and/or make-up solvent can be transferred as streams 161, 163, 165 to solvent drum 160 (in the embodiment of FIG. 1, both condensed overhead vapor streams and make-up solvent are transferred to the solvent drum). A liquid effluent 165 withdrawn from solvent drum 160 is combined with an effluent 193 of the mother-liquor drum 192 and then transferred to oxidation reactor 110, Accordingly, in certain embodiments as otherwise described herein, the solvent drum contains solvent monocarboxylic acid (e.g., acetic acid), In certain such embodiments, the solvent drum further contains one or more additional by-products selected from monocarboxylic acid solvent reaction products, water, para-xylene and partial or intermediate oxidation products thereof, and bromine and reaction products thereof. For example, in certain embodiments as otherwise described herein, the solvent drum contains acetic acid, methyl acetate, methyl bromide, and water.

A liquid effluent 167 withdrawn from solvent drum 160 is cooled in a heat exchanger 162 to form a cooled solvent stream 169, a portion of which is directed to high-pressure absorber 380 as second solvent-rich scrubbing stream 381. Accordingly, in certain embodiments as otherwise described herein, the second solvent-rich scrubbing stream comprises a liquid effluent of a solvent drum (e.g., containing acetic acid).

In certain embodiments as otherwise described herein, the second solvent-rich scrubbing stream comprises at least 80 wt. % (e.g., at least 85 wt. %, or at least 90 wt. %, or at least 95 wt. %) acetic acid. In certain such embodiments, the second solvent-rich scrubbing stream comprises further comprises one or more additional by-products selected from monocarboxylic acid solvent reaction products, water, para-xylene and partial or intermediate oxidation products thereof, and bromine and reaction products thereof, present in the second solvent-rich scrubbed stream in a combined amount up to 20 wt. % (e.g., 1-10 wt. %, or 5-15 wt. %, or 10-20 wt. %). For example, in certain embodiments as otherwise described herein, the second solvent-rich scrubbing stream comprises acetic acid, methyl acetate, methyl bromide, and water, present in the second solvent-rich scrubbing stream in a combined amount of at least 85 wt. % (e.g., at least 90 wt. %, or at least 95 wt. %, or at least 97.5 wt. %).

In certain embodiments as otherwise described herein, the process includes cooling at least a portion of a liquid effluent of a solvent drum (e.g., containing acetic acid) to form the second solvent-rich scrubbing stream. In certain embodiments as otherwise described herein, cooling at least a portion of the liquid effluent of the solvent drum comprises heat-exchange with a coolant stream having a temperature that is at least 2° C. (e.g., at least 3° C.) higher than the temperature of the cooled spent stream. In certain embodiments, the coolant stream comprises process cooling water having a temperature of 30-40° C. (e.g., 30-36° C., or 30-34° C.). The present inventors note that such temperatures, typical of process cooling water, limit the achievable temperature of the second solvent-rich scrubbing stream to temperatures higher than 30° C., for example, 32-43° C., or 32-39° C., or 32-37° C.

Advantageously, the present inventors have determined that by cooling the second solvent-rich scrubbing stream by heat-exchange with the cooled spent stream from the low-pressure scrubber, recovery of by-products of the substituted aromatic hydrocarbon oxidation reaction (e.g., acetic acid, methyl acetate, para-xylene) from the vapor stream in a high-pressure absorber can be improved. Accordingly, in certain embodiments as otherwise described herein, the process includes cooling, by heat exchange with at least a portion of the cooled spent stream, the second solvent-rich scrubbing stream, and then contacting the second vapor stream with the cooled second solvent-rich scrubbing stream in the high-pressure absorber. In certain such embodiments, the temperature of the cooled second vapor stream is at most 30° C. (e.g., 22-29° C., or 22-28° C., or 22-27° C.). In certain such embodiments, the second vapor stream is also cooled by heat-exchange with at least a portion of the cooled spent stream. In certain embodiments as otherwise described, the contacting is conducted at a pressure within the range of 6-15 barg (e.g., 6-9 barg, or 8-11 barg, or 10-13 berg, or 12-15 barg).

In certain embodiments as otherwise described herein, a warmed spent stream (i.e., comprising the heat-exchanged product of the cooled spent stream) is recycled to the low-pressure scrubber (e.g., to low-pressure scrubber 430, as make-up stream 439). In other embodiments, the warmed spent stream is transferred to a wastewater treatment zone.

In the embodiment of FIG. 1, a portion of a liquid effluent 373 withdrawn from drum 372 is directed to high-pressure absorber 380 as second water-rich scrubbing stream 383. Accordingly, in certain embodiments as otherwise described herein, the second water-rich scrubbing stream introduced to the high-pressure absorber comprises at least a portion of the water-rich condensate formed in the condensing zone. In certain embodiments as otherwise described herein, the second water-rich scrubbing stream comprises at least 85 wt. % (e.g., at least 90 wt. %, or at least 95 wt. %, or at least 97.5 wt. %) water. In certain embodiments as otherwise described herein, the second water-rich scrubbing stream comprises one or more by-products of the substituted aromatic hydrocarbon oxidation reaction selected from acetic acid, methyl acetate, and methanol. In certain embodiments as otherwise described herein, the second water-rich scrubbing stream comprises one or more of methyl acetate, methanol, and acetic acid, present in a combined amount of 1-10 wt. % (e.g., 1-8 wt %, or 1-6 wt. %, or 1-4 wt. %) of the stream.

The second vapor stream 377, optionally further cooled in a second heat exchanger (not shown) by indirect contact with at least a portion of the cooled spent stream 187, the second solvent-rich scrubbing stream 381, optionally further cooled in a second heat exchanger (not shown) by indirect contact with at least a portion of the cooled spent stream 187, and the water-liquid stream 383 are introduced to high-pressure absorber. In the high-pressure absorber 380, the second vapor stream 377 is contacted with the second solvent-rich scrubbing stream 381 and the second water-rich scrubbing stream 383 to form a second scrubbed vapor stream 385 comprising a reduced amount of one or more by-products of the substituted aromatic hydrocarbon oxidation reaction (i.e., relative to the second vapor stream 377).

In certain embodiments as otherwise described herein, the second scrubbed vapor stream comprises a reduced amount of one or more by-products of the substituted aromatic hydrocarbon oxidation reaction selected from monocarboxylic acid solvent and reaction products thereof and para-xylene and partial or intermediate oxidation products thereof. For example, in certain such embodiments, the second scrubbed vapor stream comprises a reduced amount of one or more by-products selected from acetic acid, methyl acetate, methanol, para-xylene and partial or intermediate oxidation products thereof. In certain embodiments as otherwise described herein, the second scrubbed vapor stream comprises a combined amount of acetic acid, methyl acetate, and para-xylene that is at most 20% (e.g., at most 15%, or at most 10%, or at most 5%) of a combined amount of acetic acid, methyl acetate, and para-xylene present in the second vapor stream.

A liquid effluent 387 of the high-pressure absorber 380 including one or more by-products of the substituted aromatic hydrocarbon oxidation reaction can be transferred (not shown) to the oxidation reactor 110. Accordingly, in certain embodiments as otherwise described herein, at least a portion of a liquid effluent of the high-pressure absorber including one or more by-products of the substituted aromatic hydrocarbon oxidation reaction is transferred to a reaction zone capable of performing the substituted aromatic hydrocarbon reaction. In certain such embodiments, the liquid effluent is directly transferred to the reaction zone. Of course, in other embodiments, the liquid effluent is indirectly transferred to the reaction zone. For example, in certain such embodiments, the liquid effluent is transferred to a mother-liquor drum, and then an effluent of the mother-liquid drum is transferred to the reaction zone.

The second scrubbed vapor stream 385 is heated in preheater 392 to form a preheated stream 393, which is oxidized in oxidation unit 394 to produce an oxidized high-pressure gas stream 395. The present inventors note that unrecovered by-products of the substituted aromatic hydrocarbon oxidation reaction including starting material, solvent, and solvent reaction products (e.g., acetic acid, methyl acetate, and para-xylene) present in the second scrubbed vapor stream are effectively removed from the manufacturing process by oxidation, and accordingly must be "made up" with fresh feed. The present inventors moreover note that, accordingly, improved recovery of such by-products by cooling one or more streams directed to a high-pressure absorber as described herein can desirably decrease the amounts of starting material and/or make-up solvent required by the process.

Energy from the oxidized high-pressure gas stream 395 is converted to work in expander 400, which work is converted to electrical energy by generator 420. Expanded gas from the expander is transferred as first vapor stream 421 to low-pressure scrubber 430 and contacted with the first water-rich scrubbing stream 435 to form a first scrubbed vapor stream

433 comprising a reduced amount of bromine (e.g., suitable for release to atmosphere) and a cooled spent stream 431 (e.g., suitable to cool one or more process streams to a temperature lower than achievable with typical process cooling water).

In the embodiment of FIG. 1, a portion of the liquid effluent 373 withdrawn from drum 372 is cooled in a heat exchanger 374 to form a water-rich liquid stream 461. Accordingly, in certain embodiments as otherwise described herein, the water-rich liquid stream introduced to the solvent recovery zone comprises at least a portion of the water-rich condensate formed in the condensing zone. In certain embodiments as otherwise described herein, the water-rich liquid stream comprises at least 85 wt. % (e.g., at least 90 wt. %, or at least 95 wt. %, or at least 97.5 wt. %) water. In certain embodiments as otherwise described herein, the water-rich liquid stream comprises one or more by-products of the substituted aromatic hydrocarbon oxidation reaction selected from monocarboxylic acid solvent and reaction products thereof. For example, in certain embodiments, the water-rich liquid stream comprises one or more by-products selected from acetic acid, methyl acetate, and methanol. In certain embodiments as otherwise described herein, the water-rich liquid stream comprises one or more of methyl acetate, methanol, and acetic acid, present in a combined amount of 1-10 wt. % (e.g., 1-8 wt. %, or 1-6 wt. %, or 1-4 wt. %) of the stream.

In certain embodiments as otherwise described herein, cooling at least a portion of the water-rich condensate comprises heat-exchange with a coolant stream having a temperature that is at least 2° C. (e.g., at least 3° C.) higher than the temperature of the cooled spent stream. In certain embodiments, the coolant stream comprises process cooling water having a temperature of 30-40° C. (e.g., 30-36° C., or 30-34° C.). The present inventors note that such temperatures, typical of process cooling water, limit the achievable temperature of the water-rich liquid stream to temperatures higher than 30° C., for example, 32-43° C., or 32-39° C., or 32-37° C.

Advantageously, the present inventors have determined that by cooling the water-rich liquid stream by heat-exchange with the cooled spent stream from the low-pressure scrubber, recovery of by-products of the substituted aromatic hydrocarbon oxidation reaction (e.g., acetic acid, methyl acetate) from the water-rich liquid stream in a reverse osmosis unit can be improved. Accordingly, in certain embodiments as otherwise described herein, the process includes cooling, by heat exchange with at least a portion of the cooled spent stream, the water-rich liquid stream to form a cooled water-rich liquid stream, and then separating the cooled water-rich liquid stream by reverse osmosis in the solvent recovery zone. In certain such embodiments, the temperature of the cooled water-rich liquid stream is at most 30° C. (e.g., 22-29° C., or 22-28° C., or 22-27° C.).

In certain embodiments as otherwise described herein, a warmed spent stream (i.e., comprising the heat-exchanged product of the cooled spent stream) is recycled to the low-pressure scrubber (e.g., to low-pressure scrubber 430, as make-up stream 439). In other embodiments, the warmed spent stream is transferred to a wastewater treatment zone.

The water-rich liquid stream 461, optionally further cooled in a second heat exchanger (not shown) by indirect contact with at least a portion of the cooled spent stream 187, is separated in reverse osmosis unit 460 to form a by-product stream 463 and a purified stream 465 comprising a reduced amount of one or more by-products of the substituted aromatic hydrocarbon reaction (i.e., relative to the water-rich liquid stream 461).

In certain embodiments as otherwise described herein, the purified stream comprises a reduced amount of one or more by-products of the substituted aromatic hydrocarbon oxidation reaction selected from monocarboxylic acid solvent and reaction products thereof. For example, in certain embodiments, the purified stream comprises one or more by-products selected from acetic acid, methanol, and methyl acetate. In certain embodiments as otherwise described herein, the second scrubbed vapor stream comprises a combined amount of acetic acid, methanol, and methyl acetate that is at most 15% (e.g., at most 12.5%, or at most 10%, or at most 5%) of a combined amount of acetic acid, methanol, and methyl acetate in the second vapor stream. In certain embodiments as otherwise described herein, the purified stream comprises at least 95 wt. % (e.g., at least 97.5 wt. %, or at least 99 wt %, or at least 99.5 wt. %) water.

In certain embodiments as otherwise described herein, one or more by-products of the substituted aromatic hydrocarbon oxidation reaction selected from acetic acid, methanol, and methyl acetate are present in the by-product stream in a combined amount of at least 90 wt. % (e.g., at least 95 wt. %, or at least 99 wt. %).

In certain embodiments as otherwise described herein, at least a portion of the by-product stream including one or more by-products of the substituted aromatic hydrocarbon oxidation reaction to a reactor zone capable of performing the substituted aromatic hydrocarbon reaction.

The by-product stream 463 can be transferred (not shown) to the oxidation reactor 110. Accordingly, in certain embodiments as otherwise described herein, at least a portion of the by-product stream including one or more by-products of the substituted aromatic hydrocarbon oxidation reaction is transferred to a reaction zone capable of performing the substituted aromatic hydrocarbon reaction. In certain such embodiments, the by-product stream is directly transferred to the reaction zone. Of course, in other embodiments, the by-product stream is indirectly transferred to the reaction zone. For example, in certain such embodiments, the by-product stream is transferred to a mother-liquor drum, and then an effluent of the mother-liquid drum is transferred to the reaction zone.

The purified stream 465 can be transferred (not shown) to a wastewater treatment zone (e.g., including one or more of aerobic treatment and anaerobic treatment) to produce a treated wastewater stream that can be released to the environment. The present inventors note that unrecovered by-products of the substituted aromatic hydrocarbon oxidation reaction including starting material, solvent, and solvent reaction products (e.g., acetic acid, methyl acetate, and para-xylene) present in the purified stream are effectively removed from the manufacturing process by wastewater treatment (e.g., including aerobic or anaerobic digestion), and accordingly must be "made up" with fresh feed. The present inventors moreover note that, accordingly, improved recovery of such by-products by cooling a stream directed to a solvent recovery zone including a reverse osmosis unit as described herein can desirably decrease the amounts of starting material and/or make-up solvent required by the process.

EXAMPLES

The Examples that follow are illustrative of specific embodiments of the invention, and various uses thereof.

They are set forth for explanatory purposes only, and are not to be taken as limiting the invention.

Example 1. High Pressure Absorption with Cooled Feedstreams

Recovery of para-xylene and methyl acetate from a vapor stream in a high-pressure absorber was modeled with ASPEN Plus (Aspen Technology Inc., Bedford, MA). In Runs 1-9, the temperature of the vapor stream and the acetic acid scrubbing liquid stream introduced to the absorber were independently varied. The amounts of para-xylene and methyl acetate remaining in the scrubbed vapor stream withdrawn from the top of the absorber, normalized to Run 1, are shown in Table 1, below.

TABLE 1

| | High-Pressure Absorber Recovery | | | |
| --- | --- | --- | --- | --- |
| Run | Vapor Stream Temp. (° C.) | Scrubbing Liquid Temp. (° C.) | Unrecovered Methyl Acetate (relative to Run 1) | Unrecovered para-xylene (relative to Run 1) |
| 1 | 40 | 40 | 100% | 100% |
| 2 | 35 | 40 | 74% | 49% |
| 3 | 30 | 40 | 58% | 27% |
| 4 | 30 | 30 | 53% | 24% |
| 5 | 30 | 25 | 50% | 22% |
| 6 | 35 | 35 | 72% | 47% |
| 7 | 40 | 35 | 98% | 97% |
| 8 | 40 | 30 | 95% | 93% |
| 9 | 40 | 25 | 92% | 89% |

As shown in Table 1, further cooling of the vapor stream and/or the acetic acid scrubbing liquid stream introduced to a high-pressure absorber increases recovery of reaction by-products of a substituted aromatic hydrocarbon oxidation reaction including methyl acetate and para-xylene.

Example 2. Reverse Osmosis Separation of Cooled Feedstream

Figure 2:
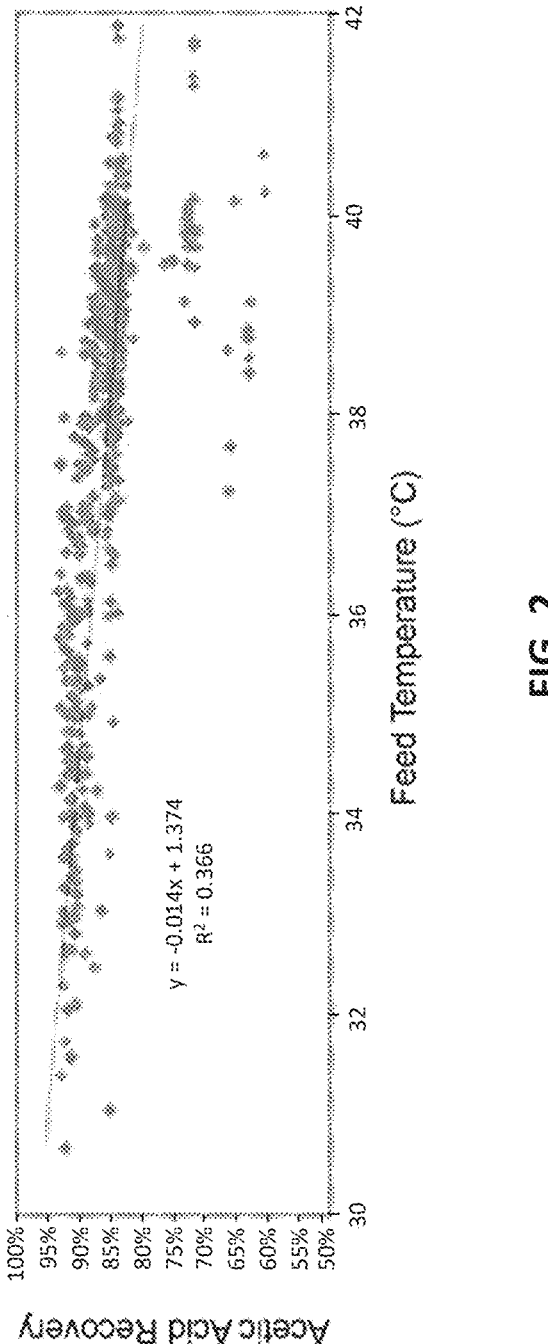
FIG. 2 is a plot depicting the effect of feed temperature on recovery efficiency of acetic acid by reverse osmosis according to certain embodiments of the disclosure.

Historical data of acetic acid recovery from a water-rich stream was compiled and analyzed to determine the effect of feedstream temperature on acetic acid recovery by reverse osmosis. The results, shown in FIG. 2, demonstrate that acetic acid recovery can be improved to greater than 90% by lowering the temperature of the water-rich stream (e.g., towards 30° C.).

Additional aspects of the disclosure are provided by the following enumerated embodiments, which can be combined in any number and in any fashion that is not technically or logically inconsistent.

Embodiment 1. A process for recovering by-products of a substituted aromatic hydrocarbon oxidation reaction, comprising in a low-pressure scrubber, contacting a first water-rich scrubbing stream with a first vapor stream comprising bromine to form a cooled spent stream and a first scrubbed vapor stream, the first scrubbed vapor stream comprising a reduced amount of bromine relative to the first vapor stream; and in a high-pressure absorber, contacting a second vapor stream comprising one or more by-products of the substituted aromatic hydrocarbon oxidation reaction with a second solvent-rich scrubbing stream to form a second scrubbed vapor stream, the second scrubbed vapor stream comprising a reduced amount of one or more by-products relative to the second vapor stream, wherein, before introduction to the high-pressure absorber, at least one of the second vapor stream and the second solvent-rich scrubbing stream is cooled by heat-exchange with at least a portion of the cooled spent stream.

Embodiment 2. The process of embodiment 1, further comprising transferring (e.g., directly or indirectly) at least a portion of a liquid effluent of the high-pressure absorber including one or more by-products of the substituted aromatic hydrocarbon oxidation reaction to a reaction zone capable of performing the substituted aromatic hydrocarbon oxidation reaction.

Embodiment 3. The process of embodiment 1 or embodiment 2, further comprising contacting the second vapor stream with a second water-rich scrubbing stream in the high-pressure absorber.

Embodiment 4. The process of any of embodiments 1-3, comprising cooling, by heat exchange with at least a portion of the cooled spent stream, the second vapor stream to form a cooled second vapor stream; and then contacting the cooled second vapor stream with the second solvent-rich scrubbing stream in the high-pressure absorber.

Embodiment 5. The process of embodiment 4, further comprising in a reaction zone, oxidizing a feedstock comprising a substituted aromatic hydrocarbon in the presence of an oxidation catalyst and monocarboxylic acid solvent under reaction conditions suitable to form crude aromatic carboxylic acid;

in a fractionation zone, separating at least a portion of a vapor effluent of the reaction zone to form a bottoms stream and a vapor overhead stream, the vapor overhead stream comprising steam and one or more additional by-products of the substituted aromatic hydrocarbon oxidation reaction;

in a condensing zone, condensing a portion of the vapor overhead stream to form a water-rich condensate; and cooling at least a portion of a vapor effluent of the condensing zone including one or more by-products to form the second vapor stream.

Embodiment 6. The process of embodiment 5, wherein cooling at least a portion of the vapor effluent comprises heat-exchange with a coolant stream having a temperature that is at least 2° C. (e.g., at least 3° C.) higher than the temperature of the cooled spent stream.

Embodiment 7. The process of any of embodiments 1-3, comprising cooling, by heat exchange with at least a portion of the cooled spent stream, the second solvent-rich scrubbing stream to form a cooled second solvent-rich scrubbing stream; and then contacting the second vapor stream with the cooled second solvent-rich scrubbing stream in the high-pressure absorber.

Embodiment 8. The process of embodiment 7, further comprising cooling at least a portion of a liquid effluent of a solvent drum (e.g., containing acetic acid) to form the second solvent-rich scrubbing stream.

Embodiment 9. The process of embodiment 8, wherein cooling at least a portion of the liquid effluent comprises heat-exchange with a coolant stream having a temperature that is at least 2° C. (e.g., at least 3° C.) higher than the temperature of the cooled spent stream.

Embodiment 10. The process of any of embodiments 1-9, wherein the first vapor stream comprises at least a portion of the second scrubbed vapor stream.

Embodiment 11. The process of embodiment 10, further comprising in a preheating zone, heating at least a portion of the second scrubbed vapor stream to form a preheated vapor stream;

in an oxidation unit, oxidizing at least a portion of the preheated vapor stream to produce an oxidized high-pressure vapor stream; and in an expander, expanding at least a portion of the oxidized high-pressure vapor stream to form the first vapor stream.

Embodiment 12. The process of any of embodiments 1-11, further comprising in a solvent recovery zone, separating at least a portion of a water-rich liquid stream comprising one or more by-products of the substituted aromatic hydrocarbon oxidation reaction by reverse osmosis to form a by-product stream and a purified stream, the purified stream comprising a reduced amount of the one or more by-products relative to the water-rich liquid stream, wherein, before introduction to the recovery zone, the water-rich liquid stream is cooled by heat-exchange with at least a portion of the cooled spent stream.

Embodiment 13. A process for recovering by-products of a substituted aromatic hydrocarbon oxidation reaction, comprising in a low-pressure scrubber, contacting a first water-rich scrubbing stream with a first vapor stream comprising bromine to form a cooled spent stream and a first scrubbed vapor stream, the first scrubbed vapor stream comprising a reduced amount of bromine relative to the first vapor stream; and in a solvent recovery zone, separating at least a portion of a water-rich liquid stream comprising one or more by-products of the substituted aromatic hydrocarbon oxidation reaction by reverse osmosis to form a by-product stream and a purified stream, the purified stream comprising a reduced amount of the one or more by-products relative to the water-rich liquid stream, wherein, before introduction to the recovery zone, the water-rich liquid stream is cooled by heat-exchange with at least a portion of the cooled spent stream.

Embodiment 14. The process of embodiment 12 or embodiment 13, further comprising transferring (e.g., directly or indirectly) at least a portion of the byproduct stream including one or more by-products of the substituted aromatic hydrocarbon oxidation reaction to a reaction zone capable of performing the substituted aromatic hydrocarbon oxidation reaction.

Embodiment 15. The process of any of embodiments 12-14, further comprising in a reaction zone, oxidizing a feedstock comprising a substituted aromatic hydrocarbon in the presence of an oxidation catalyst and monocarboxylic acid solvent under reaction conditions suitable to form crude aromatic carboxylic acid;

in a fractionation zone, separating at least a portion of a vapor effluent of the reaction zone to form a bottoms stream and a vapor overhead stream, the vapor overhead stream comprising steam and one or more additional by-products of the substituted aromatic hydrocarbon oxidation reaction;

in a condensing zone, condensing a portion of the vapor overhead stream to form a water-rich condensate comprising one or more by-products; and cooling at least a portion of the water-rich condensate including one or more by-products to form the water-rich liquid stream.

Embodiment 16. The process of embodiment 15, wherein cooling at least a portion of the water-rich condensate comprises heat-exchange with a coolant stream having a temperature that is at least 2° C. (e.g., at least 3° C.) higher than the temperature of the cooled spent stream.

Embodiment 17. The process of any of embodiments 1-16, further comprising releasing at least a portion of the first scrubbed vapor stream to atmosphere.

Embodiment 18. The process of any of embodiments 1-17, wherein the first water-rich scrubbing stream has a temperature of 32-43° C.

Embodiment 19. The process of any of embodiments 1-18, wherein the temperature of the cooled spent stream is at least 2° C. (e.g., at least 3° C.) lower than the temperature of the first water-rich scrubbing stream.

Embodiment 20. The process of any of embodiments 1-19, wherein the substituted aromatic hydrocarbon oxidation reaction is oxidation of para-xylene to form terephthalic acid.

Embodiment 21. The process of any of embodiments 1-20, wherein the one or more by-products include acetic acid, methyl acetate, methanol, and/or para-xylene.

Embodiment 22. A system for recovering by-products of a substituted aromatic hydrocarbon oxidation reaction, comprising a low-pressure scrubber capable of contacting a first water-rich scrubbing stream with a first vapor stream comprising bromine to form a cooled spent stream and a first scrubbed vapor stream, the first scrubbed vapor stream comprising a reduced amount of bromine relative to the first vapor stream;

a heat exchanger capable of cooling, by heat exchange with at least a portion of the cooled spent stream, a second solvent-rich scrubbing stream to form a cooled second solvent-rich scrubbing stream; and a high-pressure absorber capable of contacting a second vapor stream comprising one or more by-products of the substituted aromatic hydrocarbon oxidation reaction with the cooled second solvent-rich scrubbing stream to form a second scrubbed vapor stream, the second scrubbed vapor stream comprising a reduced amount of one or more by-products relative to the second vapor stream.

Embodiment 23. A system for recovering by-products of a substituted aromatic hydrocarbon oxidation reaction, comprising a low-pressure scrubber capable of contacting a first water-rich scrubbing stream with a first vapor stream comprising bromine to form a cooled spent stream and a first scrubbed vapor stream, the first scrubbed vapor stream comprising a reduced amount of bromine relative to the first vapor stream;

a heat exchanger capable of cooling, by heat exchange with at least a portion of the cooled spent stream, a second vapor stream comprising one or more by-products of the substituted aromatic hydrocarbon oxidation reaction to form a cooled second vapor stream; and a high-pressure absorber capable of contacting the cooled second vapor stream with a second solvent-rich scrubbing stream to form a second scrubbed vapor stream, the second scrubbed vapor stream comprising a reduced amount of one or more by-products relative to the second vapor stream.

Embodiment 24. A system for recovering by-products of a substituted aromatic hydrocarbon oxidation reaction, comprising a low-pressure scrubber capable of contacting a first water-rich scrubbing stream with a first vapor stream comprising bromine to form a cooled spent stream and a first scrubbed vapor stream, the first scrubbed vapor stream comprising a reduced amount of bromine relative to the first vapor stream;

a heat exchanger capable of cooling, by heat exchange with at least a portion of the cooled spent stream, a water-rich liquid stream comprising one or more by-products of the substituted aromatic hydrocarbon oxidation reaction to form a cooled water-rich liquid stream; and a reverse osmosis unit capable of separating at least a portion of the cooled water-rich liquid stream by reverse osmosis to form a by-product stream and a purified stream, the purified stream comprising a reduced amount of one or more by-products relative to the water-rich liquid stream.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for recovering by-products of a substituted aromatic hydrocarbon oxidation reaction, comprising in a low-pressure scrubber, operating at a pressure in the range of 0-0.5 barg, contacting a first water-rich scrubbing stream with a first vapor stream comprising bromine to form a cooled spent stream and a first scrubbed vapor stream, the first scrubbed vapor stream comprising a reduced amount of bromine relative to the first vapor stream, wherein a temperature of the cooled spent stream is at least 2° C. lower than a temperature of the first water-rich scrubbing stream;

the process further comprising one or both of a) in a high-pressure absorber, contacting a second vapor stream comprising one or more by-products of the substituted aromatic hydrocarbon oxidation reaction with a second solvent-rich scrubbing stream to form a second scrubbed vapor stream, the second scrubbed vapor stream comprising a reduced amount of one or more by-products relative to the second vapor stream, wherein, before introduction to the high-pressure absorber, at least one of the second vapor stream and the second solvent-rich scrubbing stream is cooled by heat-exchange with at least a portion of the cooled spent stream; and b) in a solvent recovery zone, separating at least a portion of a water-rich liquid stream comprising one or more by-products of the substituted aromatic hydrocarbon oxidation reaction by reverse osmosis to form a by-product stream and a purified stream, the purified stream comprising a reduced amount of the one or more by-products relative to the water-rich liquid stream, wherein, before introduction to the recovery zone, the water-rich liquid stream is cooled by heat-exchange with at least a portion of the cooled spent stream.

2. The process of claim 1, further comprising transferring at least a portion of a liquid effluent of the high-pressure absorber including one or more by-products of the substituted aromatic hydrocarbon oxidation reaction to a reaction zone capable of performing the substituted aromatic hydrocarbon oxidation reaction.

3. The process of claim 1, further comprising contacting the second vapor stream with a second water-rich scrubbing stream in the high-pressure absorber.

4. The process of claim 1, comprising
cooling, by heat exchange with at least a portion of the cooled spent stream, the second vapor stream to form a cooled second vapor stream; and then
contacting the cooled second vapor stream with the second solvent-rich scrubbing stream in the high-pressure absorber.

5. The process of claim 4, further comprising
in a reaction zone, oxidizing a feedstock comprising a substituted aromatic hydrocarbon in the presence of an oxidation catalyst and monocarboxylic acid solvent under reaction conditions suitable to form crude aromatic carboxylic acid;
in a fractionation zone, separating at least a portion of a vapor effluent of the reaction zone to form a bottoms stream and a vapor overhead stream, the vapor overhead stream comprising steam and one or more additional by-products of the substituted aromatic hydrocarbon oxidation reaction;
in a condensing zone, condensing a portion of the vapor overhead stream to form a water-rich condensate; and
cooling at least a portion of a vapor effluent of the condensing zone including one or more by-products to form the second vapor stream.

6. The process of claim 5, wherein cooling at least a portion of the vapor effluent comprises heat-exchange with a coolant stream having a temperature that is at least 2° C. higher than the temperature of the cooled spent stream.

7. The process of claim 1, comprising
cooling, by heat exchange with at least a portion of the cooled spent stream, the second solvent-rich scrubbing stream to form a cooled second solvent-rich scrubbing stream; and then
contacting the second vapor stream with the cooled second solvent-rich scrubbing stream in the high-pressure absorber.

8. The process of claim 7, further comprising cooling at least a portion of a liquid effluent of a solvent drum to form the second solvent-rich scrubbing stream.

9. The process of claim 8, wherein cooling at least a portion of the liquid effluent comprises heat-exchange with a coolant stream having a temperature that is at least 2° C. higher than the temperature of the cooled spent stream.

10. The process of claim 1, comprising
cooling, by heat exchange with at least a portion of the cooled spent stream, the water-rich liquid stream to form a cooled water-rich liquid stream; and then separating the cooled water-rich liquid stream by reverse osmosis in the solvent recovery zone.

11. The process of claim 10, further comprising transferring at least a portion of the byproduct stream including one or more by-products of the substituted aromatic hydrocarbon oxidation reaction to a reaction zone capable of performing the substituted aromatic hydrocarbon oxidation reaction.

12. The process of claim 10, further comprising
in a reaction zone, oxidizing a feedstock comprising a substituted aromatic hydrocarbon in the presence of an oxidation catalyst and monocarboxylic acid solvent under reaction conditions suitable to form crude aromatic carboxylic acid;
in a fractionation zone, separating at least a portion of a vapor effluent of the reaction zone to form a bottoms stream and a vapor overhead stream, the vapor overhead stream comprising steam and one or more additional by-products of the substituted aromatic hydrocarbon oxidation reaction;
in a condensing zone, condensing a portion of the vapor overhead stream to form a water-rich condensate comprising one or more by-products; and
cooling at least a portion of the water-rich condensate including one or more by-products to form the water-rich liquid stream.

13. The process of claim 12, wherein cooling at least a portion of the water-rich condensate comprises heat-exchange with a coolant stream having a temperature that is at least 2° C. higher than the temperature of the cooled spent stream.

14. The process of claim 1, wherein the first vapor stream comprises at least a portion of the second scrubbed vapor stream.

15. The process of claim 14, further comprising
in a preheating zone, heating at least a portion of the second scrubbed vapor stream to form a preheated vapor stream;
in an oxidation unit, oxidizing at least a portion of the preheated vapor stream to produce an oxidized high-pressure vapor stream; and
in an expander, expanding at least a portion of the oxidized high-pressure vapor stream to form the first vapor stream.

16. The process of claim 1, further comprising releasing at least a portion of the first scrubbed vapor stream to atmosphere.

17. The process of claim 1, wherein the first water-rich scrubbing stream has a temperature of 32-43° C.

18. The process of claim 1, wherein the substituted aromatic hydrocarbon oxidation reaction is oxidation of para-xylene to form terephthalic acid.

19. The process of claim 1, wherein the one or more by-products include acetic acid, methyl acetate, methanol, and/or para-xylene.

20. A system for recovering by-products of a substituted aromatic hydrocarbon oxidation reaction, comprising
a low-pressure scrubber, operating at a pressure in the range of 0-0.5 barg and capable of contacting a first water-rich scrubbing stream with a first vapor stream comprising bromine to form a cooled spent stream and a first scrubbed vapor stream, the first scrubbed vapor stream comprising a reduced amount of bromine relative to the first vapor stream, wherein a temperature of the cooled spent stream is at least 2° C. lower than a temperature of the first water-rich scrubbing stream;
the system further comprising one or both of a) a high-pressure absorber capable of contacting a second vapor stream comprising one or more by-products of the substituted aromatic hydrocarbon oxidation reaction with a second solvent-rich scrubbing stream to form a second scrubbed vapor stream, the second scrubbed vapor stream comprising a reduced amount of one or more by-products relative to the second vapor stream, and at least one of a heat exchanger capable of cooling the second vapor stream before introduction to the high-pressure absorber, by heat exchange with at least a portion of the cooled spent stream; and a heat exchanger capable of cooling the second solvent-rich scrubbing stream before introduction to the high-pressure absorber, by heat exchange with at least a portion of the cooled spent stream; and b) a reverse osmosis unit capable of separating at least a portion of a water-rich liquid stream comprising one or more by-products of the substituted aromatic hydrocarbon oxidation reaction by reverse osmosis to form a by-product stream and a purified stream, the purified stream comprising a reduced amount of the one or more by-products relative to the water-rich liquid stream, and a heat exchanger capable of cooling the water-rich liquid stream before introduction to the recovery zone, by heat exchange with at least a portion of the cooled spent stream.

\* \* \* \* \*